United States Patent [19]
Hayes et al.

[11] 4,150,571
[45] Apr. 24, 1979

[54] HUMIDISTAT

[75] Inventors: Thomas E. Hayes, Goshen, Ind.;
Robert E. Emmons, Urbandale, Iowa;
Jon H. Bechtel, Goshen, Ind.

[73] Assignee: Johnson Service Company, Milwaukee, Wis.

[21] Appl. No.: 580,211

[22] Filed: May 23, 1975

Related U.S. Application Data

[63] Continuation of Ser. No. 418,440, Nov. 23, 1973, abandoned.

[51] Int. Cl.² ............................................... G01W 1/00
[52] U.S. Cl. .................................... 73/336.5; 73/337.5
[58] Field of Search ...................... 73/336.5, 337.5, 337

[56] References Cited

U.S. PATENT DOCUMENTS

| | | | |
|---|---|---|---|
| 1,961,012 | 5/1934 | Platzer | 73/336.5 |
| 2,467,929 | 4/1949 | Colt | 73/337.5 |
| 2,767,973 | 10/1956 | Terveen et al. | 73/517 R |
| 3,756,080 | 9/1973 | Young | 73/336.5 |

OTHER PUBLICATIONS

W. Ryland Hill, *Electronics in Engineering*, McGraw-Hill Book Co., Inc., 1961, pp. 303–304.

*Primary Examiner*—Anthony V. Ciarlante
*Attorney, Agent, or Firm*—Emrich, Root, O'Keefe & Lee

[57] ABSTRACT

An humidistat has an element movable in response to ambient relative humidity operatively connected to a core of a linearly variable differential transformer for moving the core. The core is supported within a body portion of the transformer for minimal friction of movement relative to the body portion. The body portion has a primary winding and two secondary windings. An oscillator excites the primary winding to provide output signals from the secondary windings proportioned to movement of the core in the body portion and, therefore, indicative of the relative humidity sensed by the element.

1 Claim, 4 Drawing Figures

HUMIDISTAT

This is a continuation of application Ser. No. 418,440, filed Nov. 23, 1973 now abandoned.

BACKGROUND OF THE INVENTION

This invention relates to a device for detecting relative humidity.

Devices for the detection of atmospheric conditions are legion. In particular, devices for the detection of relative humidity are known; such devices are often called humidistats.

One known type of humidistat uses an element having at least a portion movable in response to a sensed humidity. Often, the movement is a change in a physical dimension of the element. For example, human hair is often used as the humidity sensing element. The hair is placed under longitudinal tension by a biasing load. As the ambient humidity changes, the hair changes in length.

However, the change in length of a hair element usually is relatively small per unit length of the hair. Typical humidity responsive changes in length of such hair elements are in a range of 2%. Normally, hair movement is converted to an electrical output signal indicating humidity by means of a rheostat which has inherent friction.

It is desirable to provide constant load biasing the hair with minimal friction against hair movement over the entire range of the humidity sensing element.

SUMMARY OF THE INVENTION

Accordingly, it is an object of the invention to provide a humidistat having means responsive to the relatively small movement of a humidity sensing element under a load and with minimal friction over its entire range.

To this end the invention provides a humidistat having an element movable in response to a sensed humidity. The element is operatively connected to the movable core of a variable transformer for controlling an output from the transformer. Excitation of the transformer then provides an output signal indicative of the relative humidity sensed by the element with minimal friction of the mechanical to electrical output transducer.

A preferred embodiment of the invention additionally comprises a device for presetting an initial output signal of the transformer. The presetting device permits adjustment of the relative humidity to which the humidistat is responsive. In addition, the preferred embodiment also has adjustable means amplifying the output signal from the transformer.

DESCRIPTION OF THE DRAWINGS

A preferred embodiment which is intended to illustrate and not to limit the invention will now be described with reference to drawings, in which.

DESCRIPTION OF THE PREFERRED EMBODIMENT

Figure 1:
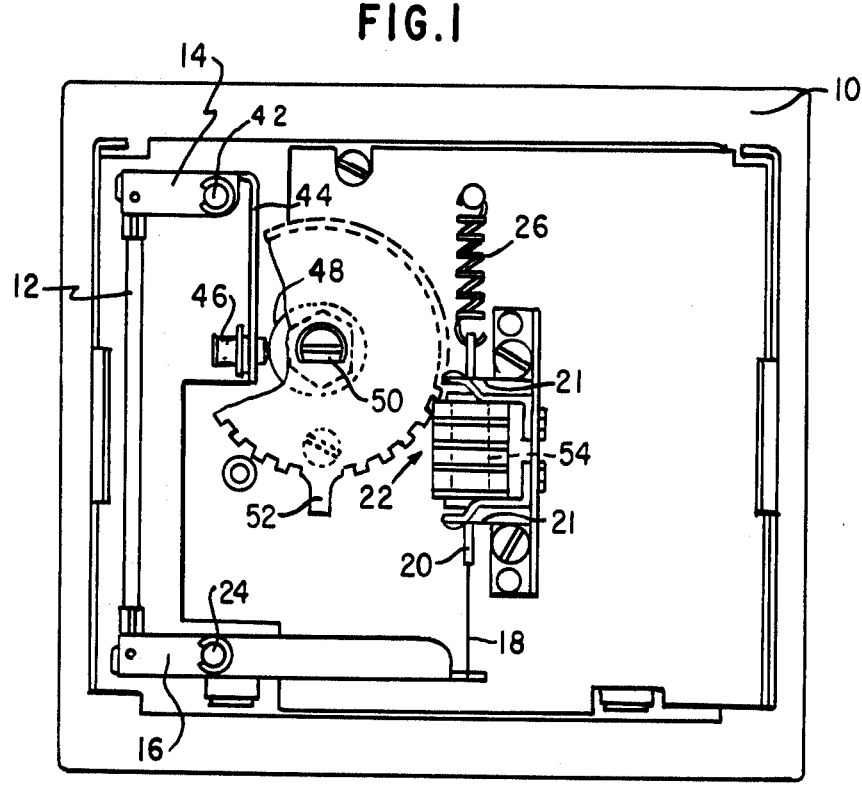
FIG. 1 is a top view of mechanical components of the embodiment.

As seen in FIG. 1, the preferred embodiment has a base 10 on which all the mechanical components of the embodiment are supported. A humidity sensing element 12 is tensioned between a support 14 and one end of a lever 16. The element may be hair or nylon or other humidity responsive substance. An end of the lever 16 opposite that to which the hair element is connected is connected to a cable 18. The lever 16 is mounted intermediate its ends on a pivot 24 extending from the base. The cable 18 is also connected to a movable core 20 of a linearly variable differential transformer having a body portion generally at 22. Core 20 is guided along the axis of transformer body 22 by two highly compliant spiders 21, one at each end of body portion 22; spiders 21 being fastened to body supports 23 for the transformer. This suspension of core 20 eliminates sliding friction between core 20 and body portion 22. Spiders 21 are formed of beryllium copper strips, such as alloy 25 of the Brush Beryllium Company and selected of a thickness of 0.002" to minimize spring constant. A tension is provided to the connected core, lever and hair by a spring 26 connected at one end to the core and at another to the base. Expansion and contraction of the length of the hair 12 in response to the changes in the humidity ambient the hair then pivots the lever 16 to move the core 20 relative to the transformer body portion at 22. This eliminates entirely the frictional load normally placed on the hair by rheostats of prior art humidistats for converting mechanical movement of the hair to an electrical output signal.

Figure 3:
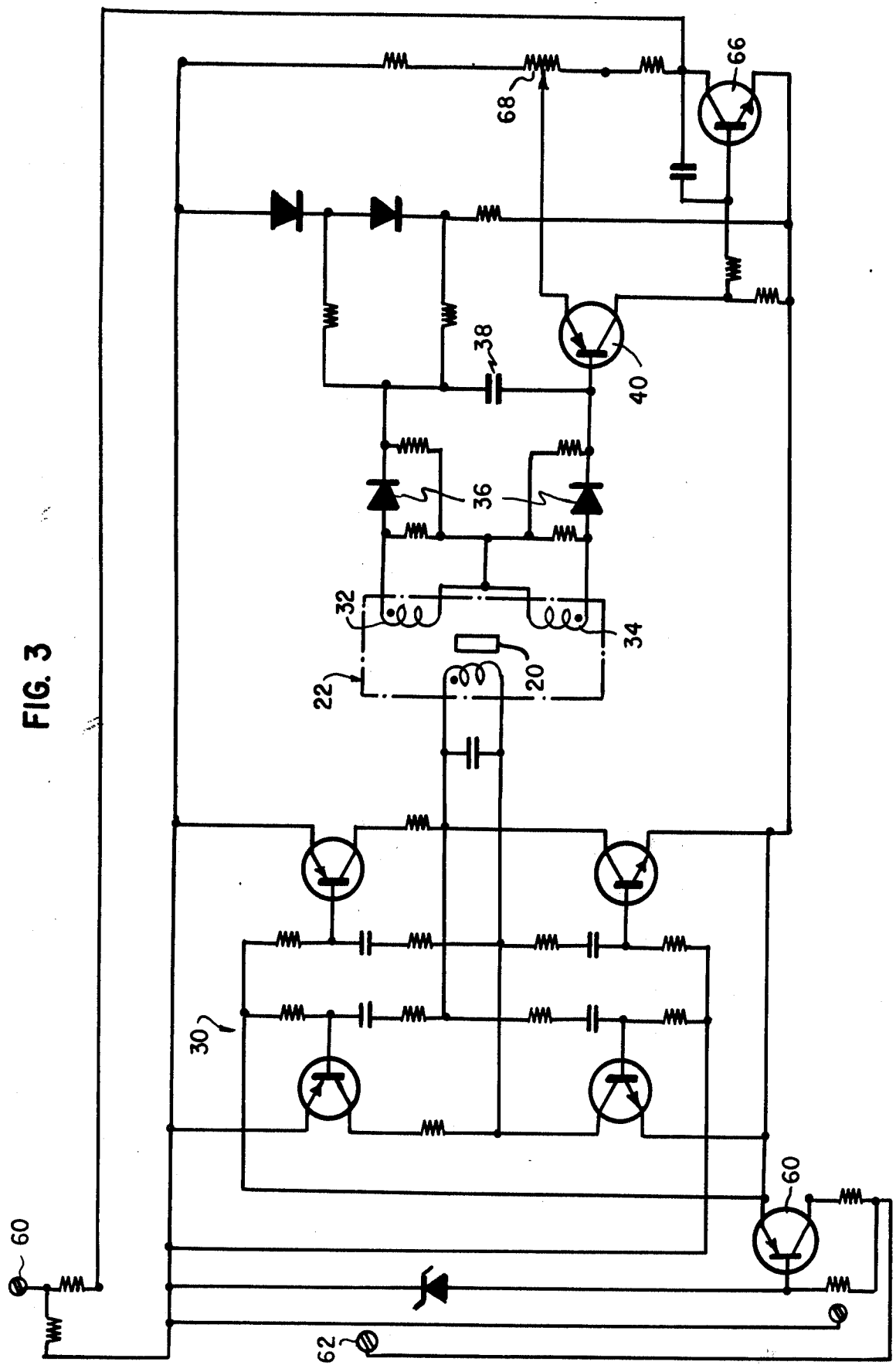
FIG. 3 is an electrical schematic of the embodiment.

Turning to FIG. 3, an oscillator of the free running multivibrator type, generally designated 30, provides an alternating current excitation to a primary winding 23 in the body portion of the transformer now shown schematically at 22. A pair of secondary windings 24 and 25 spaced from each other along the body portion of the transformer and connected in series oppositon provide like polarity signals on output leads 32 and 34 connected respectively, to one of the secondary windings. Each of the output leads 32 and 34 carry current through a diode 36 in each lead to an opposite side of a capacitor 38. The capacitor 38 is also connected to the base of a transistor 40 to control current flow through the transistor. Current from the transistor 40 is amplified by transistor 66 and is provided to an output terminal 42.

As expansion and contraction of the hair elememt 12 (FIG. 1) moves the core 20 of the transformer relative to the secondary windings 24 and 25 in the body portion of the transformer at 22, the current in one secondary winding will exceed that in the other. One of the leads 32 or 34 will conduct this greater current to capacitor 38 to provide lesser charge accumulation on the side of capacitor 38 to which the lead is connected. The resulting potential differential across the capacitor 38 will control the current flow through the transistor 40. The increased or decreased current through transistor 40 is then responsive to the humidity sensed by the element and is provided as an output signal at terminal 42. The diodes 36, capacitor 38 and transistor 40 thus form a differential discriminator responsive to the difference between transformer output signals on leads 32 and 34.

Returning to FIG. 1, the support 14 is mounted on a pivot 42 extending from base 10 and has an arm extending on each side of the pivot. One arm carries the hair element 12; the other arm 44 into engagement with a cam 48 rotatably mounted on a bolt 50 extending from the base. Rotation of the cam 48 then positions the abutment screw 46 radially of the cam to pivot support 14. Pivotal movement of the support 14 moves the hair element 12 relative to the base to position the core 20 of the transformer.

A tang 52 on a portion of the cam 48 indicates the rotational position of the cam relative to base 10. The bolt 50 may be then tightened to secure the cam in a desired, preset rotational position. The corresponding preset positioning of the support 14, hair 12, lever 16 and cable 18 presets the position of transformer core 20. Since the position of core 20 relative to the transformer body portion at 22 controls the output of the transformer, presetting the core position presets an humidity indicating transformer output relative to which the embodiment will be responsive. For example, the core of the transformer may be symmetrically positioned with respect to the spaced secondary windings in the transformer body portion to provide equal output signals from each transformer lead 32 and 34 (FIG. 3) at any particular humidity. Capacitor 38 (FIG. 3) then receives no charge differential from the transformer and a null-level signal appears at terminal 42. Changes in the humidity from that at which the core position was preset will then reposition the core to indicate an humidity relative to that at which the core position was preset. Alternatively, the hair element 12 may be exposed to a maximum or minimum humidity condition for which the embodiment is to be used, and the cam positioned to adjust the output from the transformer to a corresponding maximum or minimum output signal. Subsequent humidity indications will then be relative to this maximum or minimum reference level.

Figure 2A:
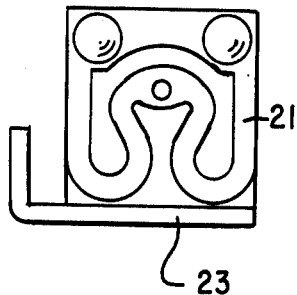
FIGS. 2 and 2A is a view partly in section of a portion of the mechanical components shown in FIG. 1.
Figure 2:
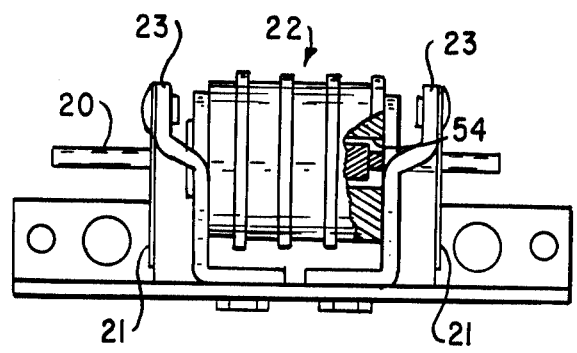

Spring 26 is mounted on the base to have its axis of spring operation aligned with the point at which the cable 18 connects to lever 16. The transformer body portion is mounted on the base to have a longitudinal axis of an internal passageway 54 aligned with a longitudinal axis of the core 20. As seen in FIG. 2, the core 20 is guided within the passageway 54 of body 22 by spiders 21, and, preferably in radially spaced coaxial alignment with the longitudinal axis of the passageway. Frictional drag of the transformer core on the transformer body portion is thus eliminated. Moreover, the core 20 preferably has relatively low mass to require a correspondingly light spring tension for its support and to have a correspondingly low inertia. The light spring tension minimizes the elastic distortion of the hair while the low inertia minimizes the energy required for core movement in response to changes in the length of the hair. Accordingly, the mechanical components of the mechanical to electrical transducer are highly responsive to humidity induced changes to the length of hair 12.

FIG. 3 also shows a power supply transistor 60 connected to a DC power input terminal 62 for controlling the power supplied to the remaining portions of the circuit.

The emitter of transistor 40 is connected to an adjustable center tap of a potentiometer 68 for adjusting the gain of the transistor. The output signal from transistor 40 is then further amplified by transistor 66, of fixed gain, and provided to the output terminal 42. A convenient indicating device, such as a voltmeter, may be connected to terminal 42 to provide a visible indication of the relative humidity sensed by the embodiment. Alternatively, a humidifier controlling the ambient humidity may be activated by the signal at output terminal 42. Adjustment of the gain potentiometer 68 then permits the embodiment to meet both the requirements of the output device as well as the expected sensitivity of the embodiment.

In the preferred embodiment shown in the figures, the core transformer at 20 and 22 is a ceramic linearly variable differential transformer having secondary windings connected in series opposition. Accordingly, when the transformer primary winding 23 is energized by a signal of approximately 15.5 volts, for example, identical voltages are induced in the secondary windings and like potentials are applied to leads 32 and 34 when the core is centered in the body and unequal voltages are induced in the secondary windings such that the potentials differ over a range of ± 0.25V DC when the core is displaced relative to the body. This transformer is commercially available from the Baso Division Johnson Service Company of Milwaukee. In this embodiment the multivibrator at 30 is of a known, saturable or square wave type operating from 16 V DC from transistor 60 to provide 15.5V DC excitation to the transformer. Transistor 40 may then be a commercially available type 2N5138 connected with a commercial potentiometer 68 of 200 ohms to provide a variable output signal gain varying the proportional band of the embodiment between 3% and 20% relative humidity. Each other discrete component shown in schematic FIG. 3 is of a commercially available type selected for proper circuit design as well understood by those in the art.

Although the preferred embodiment has been described as comprising a linearly variable differential transformer, it will be understood that transformers of non-linear response are also suitable. For example, an exponentially response transformer may be used when a logarithmic read-out is desirable. This and other changes to the preferred embodiment are intended to be within the scope of our invention, in which what we claim and desire to secure by Letters Patent of the United States is:

We claim:

1. A humidistat comprising a differential transformer having a body portion with a primary winding and first and second secondary windings circumferentially wound thereon, said body portion having a central passageway extending longitudinally thereof, a movable core member extending within said passageway for coupling said secondary windings to said primary winding, and means located at each end of said core member for resiliently supporting said core member within said passageway in a spaced relationship with an inner surface thereof, excitation means for applying an excitation signal to said primary winding for coupling over said core member to said secondary windings, said first and second secondary windings being connected in series opposition such that a preselected potential difference is provided between first and second terminals of said first and second secondary windings, respectively, whenever said core member is at a first position, a humidity sensing element for sensing humidity within a given environment, and means operatively connecting said sensing element to said core member for moving said core member relative to said windings from said first position to different positions as a function of humidity sensed by said sensing element to thereby vary the signal coupling and correspondingly the potential difference between said first and second terminals as a function of changes in the humidity from a set point value as sensed by said sensing element, and output means including amplifier means for establishing a proportional band for said humidistat, said amplifier means being connected across said terminals of said secondary windings and responsive to the potential difference between said terminals to provide a DC output signal that is indicative of the humidity within said environment relative to said set point value, and means for adjusting the gain of said amplifier means to thereby adjust the proportional band of said humidistat.

* * * * *